United States Patent
Pelcman et al.

(10) Patent No.: US 7,220,752 B2
(45) Date of Patent: May 22, 2007

(54) COMPOUNDS ACTIVE AT THE GLUCOCORTICOID RECEPTOR II

(75) Inventors: Benjamin Pelcman, Stockholm (SE); Annika Gustafsson, Ekerö (SE); Philip R. Kym, Grayslake, IL (US)

(73) Assignees: Karo Bio AB, Huddinge (SE); Abbott Laboratories, Abbott Park, IL (US)

( * ) Notice: Subject to any disclaimer, the term of this patent is extended or adjusted under 35 U.S.C. 154(b) by 396 days.

(21) Appl. No.: 10/433,015

(22) PCT Filed: Nov. 28, 2001

(86) PCT No.: PCT/IB01/02302

§ 371 (c)(1),
(2), (4) Date: Oct. 14, 2003

(87) PCT Pub. No.: WO02/43648

PCT Pub. Date: Jun. 6, 2002

(65) Prior Publication Data

US 2004/0063781 A1    Apr. 1, 2004

(30) Foreign Application Priority Data

Nov. 29, 2000 (GB) ............... 0029102.1

(51) Int. Cl.
    A61K 31/435    (2006.01)
    A61K 31/425    (2006.01)
    A61K 31/36     (2006.01)
    C07D 265/30    (2006.01)
    C07D 211/34    (2006.01)
    C07D 277/30    (2006.01)
    C07D 317/44    (2006.01)

(52) U.S. Cl. ............ 514/277; 514/317; 514/365; 514/464; 544/171; 546/239; 546/342; 548/204; 549/447

(58) Field of Classification Search ........... 544/171; 562/460; 546/239, 342; 548/204; 549/447; 514/239.5, 317, 277, 365, 464
See application file for complete search history.

(56) References Cited

FOREIGN PATENT DOCUMENTS

WO    WO 99/63976    12/1999
WO    WO 00/07972    2/2000

OTHER PUBLICATIONS

Huff, Journal of Medicinal Chemistry, vol. 34, No. 8, pp. 2305-2314, (1991).*
Cancer and Metastasis Reviews (1998), 17(1), 91-106.*
Science (1999), vol. 286, 531-537.*
FDA mulls drug to slow late-stage Alzheimer's [online], [retrieved on Sep. 23, 2003]. Retrieved from the Internet,URL;http://www.cnn.com/2003/HEALTH/conditions/09/24/alzheimers.drug.ap/index.html>.*

* cited by examiner

*Primary Examiner*—Rebecca Anderson
(74) *Attorney, Agent, or Firm*—Todd E. Garabedian; Elizabeth A. Galletta; Wiggin and Dana LLP

(57) ABSTRACT

This invention relates to novel compounds that are liver selective glucocorticoid receptor antagonists, to methods of preparing such compounds, and to methods for using such compounds in therapy and in the regulation of metabolism, especially lowering blood glucose levels. The compounds referred to are compounds according to the formula 1:

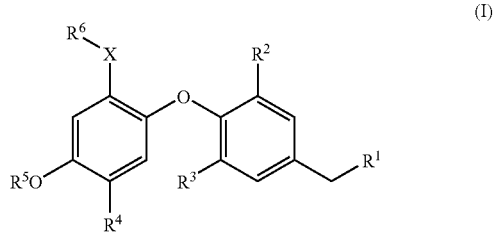

wherein the variables are as defined herein.

14 Claims, No Drawings

COMPOUNDS ACTIVE AT THE GLUCOCORTICOID RECEPTOR II

This application is a 371 of PCT/IB01/02302 filed Nov. 28, 2001.

FIELD OF THE INVENTION

This invention relates to novel compounds that are liver selective glucocorticoid receptor antagonists, to methods of preparing such compounds, and to methods for using such compounds in therapy and in the regulation of metabolism, especially lowering blood glucose levels.

BACKGROUND OF THE INVENTION

A major problem with both Type 2 and Type 1 diabetes is that there is an excessive and inappropriate production of glucose by the liver. This abnormality is the primary cause of fasting hyperglycemia and occurs in addition to defects in regulation of insulin release and in peripheral sensitivity to insulin. Thus, agents that decrease liver glucose production would be beneficial for treating both Type 2 and also Type 1 diabetes.

Intensive treatment of the hyperglycemia of Type 1 diabetes mellitus has been shown to markedly decrease the development of ocular, renal and neuropathic complications, and there is evidence that intensive treatment is also beneficial for Type 2 diabetes. The available data also indicate that most patients are currently not receiving ideal and state-of-the-art treatment for either Type 2 or Type 1 diabetes. This inadequacy exists in spite of the availability of several different types of preparations of insulin for treatment of both Type 2 and Type 1 diabetes, and of a number of additional modalities, including agents that stimulate insulin release (e.g. sulfonylureas), influence liver glucose production (e.g. metformin), affect the sensitivity to insulin (e.g. compounds interacting with the PPARγ such as troglitazone, rosiglitazone and pioglitazone) and glucose absorption (e.g. α-glucosidase inhibitors such as acarbose). In spite of the availability of several different orally active agents that lower blood glucose levels, many patients with Type 2 diabetes also require insulin for control of their blood sugar levels. Overall, insulin usage in Type 2 diabetes exceeds that for Type 1 diabetes, and there is general agreement that there is a need for additional orally active agents to treat Type 2 diabetes.

The glucocorticoids secreted from the adrenal gland (dominantly cortisol in humans) were so-named because of their ability to regulate glucose metabolism. These steroids stimulate the production of glucose in the liver by promoting gluconeogenesis, which is the biosynthesis of new glucose (i.e. not glucose from glycogen). Thus, in glucocorticoid insufficiency there is a tendency to hypoglycemia, with decreased liver glucose production. Further, development of Addison's disease in the diabetic generally leads to lowered glucose l vels. Conversely, glucocorticoid excess can provoke frank diabetes in individuals with latent diabet s mellitus, and generally aggravates glycemic control in established diabetics. Similar influences have been observed in various animal models.

The glucocorticoid receptor (GR) belongs to a large group of ligand dependent intracellular receptors, which regulate transcription of genes. The increased glucose production in response to glucocorticoids is due to effects of a number of proteins, which are GR regulated. Important among these proteins are various transaminases that convert amino acids to glucose precursors, glucose-6 phosphatase and phosphoenolpyruvate carboxy-kinase (PEPCK). Even a modest increase of PEPCK, as obtained in transgenic mice, gives rise to hyperglycemia. In mice with Type 2 diabetes and increased levels of corticosterone (the endogenous glucocorticoid of that species) there is increased expression of PEPCK. This over-expression of PEPCK can be repressed by treatment with the GR antagonist RU486 with a concomitant decrease in the hyperglycemia.

The considerations outlined above indicate that if actions of endogenous glucocorticoids on liver glucose production could be blocked in a specific manner, glycemic control could be improved for the benefit of the diabetic patients. However, to date, all means to block glucocorticoid action have been general. Thus, adrenalectomy leaves the patent with frank adrenal insufficiency and the problems of Addison's disease. Blockade of adrenal steroid production, for example by metyrapone, or of glucocorticoid action, for example with RU486 is ordinarily of limited duration of effectiveness and when it is effective also results in generalized adrenal insufficiency. Long term, compensatory ACTH hypersecretion and increased cortisol release that override the block generally overcome these treatments. By contrast, a liver-selective GR antagonist would not have these problems, but should yet counteract the increased liver glucose production in diabetes mellitus and should be useful for treatment of Type 2 diabetes.

A liver selective GR antagonist offers a number of advantages. First, it would decrease liver glucose production. This action will have a significant effect on glycemic control. In fact, excessive liver glucose production can be the major defect in Type 2 diabetes. Secondly, such a drug should enhance insulin sensitivity because of the overall improvement in the metabolic milieu and the amelioration of the hyperglycemia-induced defects in insulin action and secretion. The decreased demand on β-cell secretion, as a result of a reduction in glycemia, would retard the progressive β-cell dysfunction characteristic of Type 2 diabetes. Another advantage of GR antagonist treatment compared with sulfonylurea or insulin treatment is that the patient would run a lower risk of hypoglycemia.

Previous efforts to block glucocorticoid action in diabetes have been hampered by the fact that any compounds used would generally block glucocorticoid action in all tissues and would lead to the potential problems of glucocorticoid insufficiency, such as hypotension, shock and ultimately death if the organism is exposed to sufficiently strong stress conditions. In contrast, a liver-selective GR-antagonist with minimal effects outside the liver could be used as a front line therapy for Type 2 diabetes, or could be used in conjunction with other existing therapies.

Also, glucocorticoids are known to influence the development and maintenance of inflammation, autoimmune disease, transplant rejection, neoplasm, leukemia, lymphoma, Cushings disease, adrenal disease, renal disease, cerebrovascular ischemia, hypercalcemia, cerebral edema, thrombocytopenia, inflammatory bowel disease, wound healing, HIV infection, central nervous system disease, spinal cord tumour, glaucoma, sleep disorder, depression, anxiety disorder, atherosclerosis, hypertension, osteoporosis, occular hypertension, nephrotoxicity, infarction, endometriosis, pregnancy disorder, psychosis, Alzheimers disease, cocaine use disorder, asthma, allergic rhinitis, conjuctivitis, rheumatoid arthritis, dermatitis, eczema, osteoarthritis, hypoglycemia, hyperinsulinemia, hyperlipidemia and obesity.

DESCRIPTION OF THE INVENTION

In accordance with the present invention, compounds are provided which are active at the glucocorticoid hormone receptor, and have the general formula I:

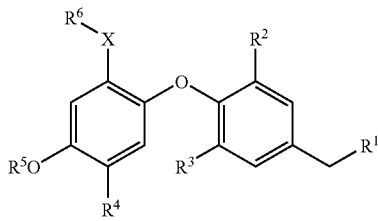

wherein:

X is selected from:
$CH_2$, $CHYR^7$, $CHYC(O)R^7$, $C=O$, $C=S$, and $C=NOR^8$;

Y is selected from:
O, S, and $NR^8$;

$R^1$ is selected from:
COOH and heteroaryl, wherein any heteroaryl residue may be optionally substituted in one or more positions independently of each other by a group selected from $C_{1-6}$-alkyl, halogen, cyano, $CF_3$, $R^8S$, $R^8S(O)_n$, and $(R^9)(R^{10})N$;

$R^2$ and $R^3$ are independently of each other selected from:
hydrogen, halogen, and $C_{1-6}$-alkyl, provided that one of $R^2$ or $R^3$ is other than hydrogen;

$R^4$ is selected from:
(i) $C_{1-6}$-alkyl, $C_{2-6}$-alkenyl and $C_{2-6}$-alkynyl, wherein any residues herein may be optionally substituted in one or more positions independently of each other by a group selected from A;
(ii) halogen, $(R^9)(R^{10})N$, $R^8C(Z)N(R^{11})$, $R^8OC(Z)N(R^{11})$, $(R^9)(R^{10})NC(Z)N(R^{11})$, $R^8S(O)_2N(R^{11})$, $(R^9)(R^{10})NS(O)_2N(R^{11})$, and $R^8SC(Z)N(R^{11})$;

$R^5$ is selected from:
(iii) $C_{1-6}$-alkyl which is substituted by a group selected from A, provided that A is not halogen;
(iv) $C_{7-12}$-alkyl, $C_{2-12}$-alkenyl and $C_{2-12}$-alkynyl, wherein any residues herein may be optionally substituted in one or more positions independently of each other by a group selected from A;
(v) $C_{1-12}$-alkyl, where one or more carbon atoms are independently of each other replaced by a group selected from Y, and where one or more carbons are optionally substituted by a group selected from A, provided that if more than one carbon is replaced by Y, the said Y groups are not directly connected to each other;

$R^6$ and $R^7$ are independently of each other selected from:
(vi) $C_{1-12}$-alkyl, $C_{3-8}$-cycloalkyl, $C_{3-8}$-heterocycloalkyl, $C_{2-6}$-alkenyl, and $C_{2-6}$-alkynyl, wherein any residues herein may be optionally substituted in one or more positions independently of each other by a group selected from A;
(vii) aryl and heteroaryl, wherein any residues herein may be optionally substituted in one or more positions independently of each other by a group selected from C;

$R^7$ is optionally selected from hydrogen;

$R^8$, $R^9$, $R^{10}$ and $R^{11}$ are independently of each other selected from: (viii) hydrogen,
(ix) $C_{1-6}$-alkyl, $C_{3-8}$-cycloalkyl, $C_{2-6}$-alkenyl, $C_{2-6}$-alkynyl, and $C_{3-8}$-heterocycloalkyl, wherein any residues herein may be optionally substituted in one or more positions independently of each other by a group selected from A;
(x) aryl and heteroaryl, wherein any residues herein may be optionally substituted in one or more positions independently of each other by a group selected from C;

or where any pair of $R^8$, $R^9$, $R^{10}$ and $R^{11}$ together with the atom or atoms to which they are bound form a ring having 3–7 ring members, and which ring optionally contain 1–3 heteroatoms, or 1–3 double bonds, and which optionally is substituted by a group selected from A;

A is selected from:
halogen, $C_{3-8}$-cycloalkyl, $C_{2-6}$-alkenyl, $C_{2-6}$-alkynyl, aryl, $C_{3-8}$-heterocycloalkyl, heteroaryl, cyano, nitro, azido, Z, $R^8O$, $R^8C(Z)$, $R^8C(Z)O$, $R^8OC(Z)$, $R^8S$, $R^8S(O)_n$, $R^8S(O)_nO$, $R^8OS(O)_n$, $(R^9)(R^{10})N$, $(R^9)(R^{10})NC(Z)$, $(R^9)(R^{10})NC(Z)O$, $R^8C(Z)N(R^{11})$, $R^8OC(Z)N(R^{11})$, $(R^9)(R^{10})NC(Z)N(R^{11})$, $(R^9)(R^{10})NS(O)_2$, $R^8S(O)_2N(R^{11})$, $(R^9)(R^{10}) NS(O)_2N(R^{11})$, and $R^8SC(Z)N(R^{11})$, wherein any $C_{1-6}$-alkyl, $C_{3-8}$-cycloalkyl, $C_{2-6}$-alkenyl, $C_{2-6}$-alkynyl, and $C_{3-8}$-heterocycloalkyl residue is optionally substituted in one or more positions independently of each other by a group selected from B, and also wherein any aryl and heteroaryl residue is optionally substituted in one or more positions independently of each other by a group selected from C; provided that if A is attached to a double or to a triple bond, or to a carbon attached to a heteroatom, A is not HO, HS, $R^9HN$, $(R^9)(R^{10})NC(Z)NH$, $(R^9)(R^{10})NS(O)_2NH$, or $R^8(O)_2NH$, and also provided that If A is attached to a double or to a triple bond, A is not Z;

B is defined as:
A, provided that if B is attached to a double or to a triple bond, or to a carbon attached to a heteroatom, B is not HO, HS, $R^9HN$, $(R^9)(R^{10})NC(Z)NH$, $(R^9)(R^{10})NS(O)_2NH$, or $R^8S(O)_2NH$, and also provided that if B is attached to a double or to a triple bond, B is not Z;

C is defined as:
A, provided that C is not Z;

Z is a substituent connected by a double bond, and is selected from:
$O=$, $S=$, $R^8N=$, $(R^9)(R^{10})NN=$, $R^8ON=$, $(R^9)(R^{10})NS(O)_2N=$, $NCN=$, $O_2NCH=$, and $(R^9)(R^{10})C=$;

n is 1 or 2;

or pharmaceutically acceptable salts, stereoisomers or prodrugs thereof.

DETAILED DESCRIPTION OF THE INVENTION

The present invention relates to compounds useful as glucocorticoid receptor modulators, and have the general formula I described above.

In that formula X may preferably be $CH_2$, $CHYR^7$, or $C=O$, and $R^1$ may preferably be COOH.

$R^2$ and $R^3$ may preferably be independently of each other, halogen or $C_{1-6}$-alkyl and more preferably both $R^2$ and $R^3$ are halogen, more preferably both $R^2$ and $R^3$ are bromine.

$R^4$ may preferably be $C_{1-6}$-alkyl and more preferably, isopropyl.

$R^5$ may preferably be $C_{1-6}$-alkyl substituted by A, provided that A is not halogen, $C_{7-12}$-alkyl, $C_{2-12}$-alkenyl or $C_{2-12}$-alkynyl.

More preferably R⁵ may be $C_{1-6}$-alkyl substituted by $(R^9)(R^{10})N$, heterocycloalkyl, aryl or heteroaryl, or $C_{7-12}$-alkyl, $C_{2-12}$-alkenyl or $C_{2-12}$-alkynyl.

R⁶ may preferably be $C_{1-12}$-alkyl, $C_{3-8}$-cycloalkyl, $C_{3-8}$-heterocycloalkyl, aryl, or heteroaryl.

More preferably R⁶ is $C_{1-12}$-alkyl, aryl or heteroaryl.

R⁹ and R¹⁰ may preferably be independently of each other hydrogen or $C_{1-6}$-alkyl, or where any pair of R⁹ and R¹⁰ together with the nitrogen to which they are bound form a ring having 5–6 ring members.

Compounds of the invention include, but are not limited to, the following. They are described in more detail in the Examples. E1 is described in Example 1, E2 in Example 2, and so on.

3,5-Dibromo-4-[5-isopropyl-2-(3-methylbenzoyl)-4-(3-methyl-3-butenyloxy)phenoxy]phenyl-acetic acid (E1);
3,5-Dibromo-4-[5-isopropyl-2-(3-methylbenzoyl)-4-(2-propynyloxy)phenoxy]phenylacetic acid (E2);
3,5-Dibromo-4-[5-isopropyl-2-(3-methylbenzoyl)-4-(pent-3-ynyloxy)phenoxy]phenylacetic acid (E3);
3,5-Dibromo-4-[5-isopropyl-4-(2-methoxyethoxy)-2-(3-methylbenzoyl)phenoxy]phenylacetic acid (E4);
3,5-Dibromo-4-[5-isopropyl-4-(2-{2-methoxyethoxy}ethoxy)-2-(3-methylbenzoyl)phenoxy]-phenylacetic acid (E5);
3,5-Dibromo-4-[5-isopropyl-4-(2-{2-[2-methoxyethoxy]ethoxy}ethoxy)-2-(3 -methylbenzoyl)-phenoxy]phenylacetic acid (E6);
3,5-Dibromo-4-[4-(7-hydroxyheptyloxy)-5-isopropyl-2-(3-methylbenzoyl)phenoxy]phenyl-acetic acid (E7);
3,5-Dibromo-4-[4-(2-ethylthioethoxy)-5-isopropyl-2-(3-methylbenzoy)phenoxy]phenylacetic acid (E8);
3,5-Dibromo-4-[4-carboxymethoxy-5-isopropyl-2-(3-methylbenzoyl)phenoxy]phenylacetic acid (E9);
3,5-Dibromo-4-[4-(5-carboxypentyloxy)-5-isopropyl-2-(3-methylbenzoyl)phenoxy]phenyl-acetic acid (E 10);
3,5-Dibromo-4-[4-benzyloxy-5-isopropyl-2-(3methylbenzoyl)phenoxy]phenylacetic acid (E11);
3,5-Dibromo-4-[4-(2-fluorobenzyloxy)-5-isopropyl-2-(3-methylbenzoyl)phenoxy]phenylacetic acid (E12);
3,5-Dibromo-4-[4-(3-fluorobenzyloxy)-5-isopropyl-2-(3-methylbenzoyl)phenoxy]phenylacetic acid (E13);
3,5-Dibromo-4-[4-(4-fluorobenzyloxy)-5-isopropyl-2-(3-methylbenzoyl)phenoxy]phenylacetic acid (E14);
3,5-Dibromo-4-[5-isopropyl-2-(3-methylbenzoyl)-4-(3-methylbenzyloxy)phenoxy]phenylacetic acid (E15);
3,5-Dibromo-4-[4-(4-tert-butoxybenzyl)-5-isopropyl-2-(3-methylbenzoyl)phenoxy]phenyl-acetic acid (E16);
3,5-Dibromo-4-[5-isopropyl-2-(3-methylbenzoyl)-4-(4-trifluoromethoxybenzyloxy)-phenoxy]phenylacetic acid (E17);
3,5-Dibromo-4-[5-isopropyl-2-(3-methylbenzoyl)-4-(3-nitrobenzyloxy)-phenoxy]phenylacetic acid (E18);
3,5-Dibromo-4-[4-(4-carboxybenzyloxy)-5-isopropyl-2-(3-methylbenzoyl)phenoxy]phenyl-acetic acid (E19);
3,5-Dibromo-4-[4-(4-carbomethoxybenzyloxy)-5-isopropyl-2-(3-methylbenzoyl)phenoxy ]-phenylacetic acid (E20);
3,5-Dibromo-4-[4-(3,5-difluorobenzyloxy)-5-isopropyl-2-(3-methylbenzoyl)phenoxy]phenylacetic acid (E21);
3,5-Dibromo-4-[4-(4bromo-2-methoxybenzyloxy)-5-isopropyl-2-(3-methylbenzoyl)-phenoxy]phenylacetic acid (E22);
3,5-Dibromo-4-[4-(2-chloro-4,5-methylenedioxybenzyloxy)-5-isopropyl-2-(3 -methylbenzoyl)-phenoxy]phenylacetic acid (E23);
3,5-Dibromo-4-[5-isopropyl-2-(3-methylbenzoyl)-4-(4pyridinylmethoxy)phenoxy]phenylacetic acid (E24);
3,5-Dibromo-4-[5-isopropyl-2-(3-methylbenzoyl)-4-(2-{4methyl-5-thiazolyl}ethoxy)-phenoxy]phenylacetic acid (E25);
3,5-Dibromo-4-[5-isopropyl-2-(3-methylbenzoyl)-4-(3-phenyl-2-propenyloxy)phenoxy]phenyl-acetic acid (E26);
3,5-Dibromo-4-[5-isopropyl-2-(3-methylbenzoyl)-4-(4-phenylbutyloxy)phenoxy]phenylacetic acid (E27);
3,5-Dibromo-4-[5-isopropyl-2-(3methylbenzoyl)-4-(2-{1-piperidino}ethoxy)phenoxy]phenyl-acetic acid (E28);
3,5-Dibromo-4-[5-isopropyl-2-(3-methylbenzoyl)-4-(2-{1-morpholino}ethoxy)phenoxy]phenyl-acetic acid (E29);

or pharmaceutically acceptable salts, stereoisomers or prodrugs thereof.

The present invention also relates to pharmaceutical compositions comprising any of the compounds of the present invention together with a pharmaceutically acceptable diluent or carrier.

The present invention also relates to processes for making the pharmaceutical compositions of the present invention.

Another embodiment of the invention is a method preventing, inhibiting or treating a disease associated with a metabolic dysfunction by administering to the mammal a therapeutically effective amount of any of the compounds or pharmaceutical compositions described herein.

Another embodiment of the invention is a method preventing, inhibiting or treating a disease, which is dependent on the expression of a glucocorticoid receptor regulated gene, by administering to the mammal a therapeutically effective amount of any of the compounds or pharmaceutical compositions described herein.

The diseases referred to comprise, but are not limited to Type 1 insulin dependent diabetes, Type 2 non-insulin dependent diabetes, Cushing's syndrome, inflammation, autoimmune disease, transplant rejection, neoplasm, leukemia, lymphoma, Cushings disease, adrenal disease, renal disease, cerebrovascular ischemia, hypercalcemia, cerebral edema, thrombocytopenia, inflammatory bowel disease, wound healing, HIV infection, central nervous system disease, spinal cord tumour, glaucoma, sleep disorder, depression, anxiety disorder, atherosclerosis, hypertension, osteoporosis, occular hypertension, nephrotoxicity, infarction, endometriosis, pregnancy disorder, psychosis, Alzheimers disease, cocaine use disorder, asthma, allergic rhinitis, conjuctivitis, rheumatoid arthritis, dermatitis, eczema, osteoarthritis, hypoglycemia, hyperinsulinemia, hyperlipidemia and obesity.

Another embodiment of the invention is a method of eliciting a glucocorticoid receptor modulating effect in a mammal in need thereof, comprising administering to the mammal a therapeutically effective amount of any of the compounds or any of the pharmaceutical compositions described herein.

One aspect of this embodiment is the method wherein the glucocorticoid receptor modulating effect is an antagonizing effect.

The compounds of the invention are glucocorticoid receptor antagonists that are preferably liver selective, and as such may be useful in the treatment of diabetes (alone or in combination with agents that stimulate insulin release such as sulfonylureas, influence liver glucose production such as metformin, affect the sensitivity to insulin such as troglitazone, or inhibit glucose absorption such as α-glucosidase inhibitors).

The compounds of the present invention in labelled form, e. g. isotopically labelled, may be used as diagnostic agents.

Further exemplifying the invention is the use of any of the compounds described above in the manufacture or preparation of a medicament for therapeutic treatment or prevention of a disease associated with a metabolism dysfunction, or a disease which is dependent on the expression of a glucocorticoid receptor regulated gene, in a mammal in need thereof. Still further exemplifying the invention is the use of any compounds described above in the manufacture or preparation of a medicament for the therapeutic treatment or prevention of Type 1 insulin dependent diabetes, Type 2 non-insulin dependent diabetes, Cushing's syndrom, inflammation, autoimmune disease, transplant rejection, neoplasm, leukemia, lymphoma, Cushings disease, adrenal disease, renal disease, cerebrovascular ischemia, hypercalcemia, cerebral edema, thrombocytopenia, inflammatory bowel disease, wound healing, HIV infection, central nervous system disease, spinal cord tumour, glaucoma, sleep disorder, depression, anxiety disorder, atherosclerosis, hypertension, osteoporosis, occular hypertension, nephrotoxicity, infarction, endometriosis, pregnancy disorder, psychosis, Alzheimers disease, cocaine use disorder, asthma, allergic rhinitis, conjuctivitis, rheumatoid arthritis, dermatitis, eczema, osteoarthritis, hypoglycemia, hyperinsulinemia, hyperlipidemia and obesity.

The compounds of the present invention can be administered in such oral dosage forms as tablets, capsules (each of which includes sustained release or timed release formulations), pills, powder, granules, elixirs, tinctures, suspensions, syrups and emulsions. Likewise, they may also be administered in intravenous (bolus or infusion), intraperitoneal, topical (e.g. ocular eyedrop), subcutaneous, intramuscular, or transdermal (e.g. patch) form, all using forms well known to those of ordinary skill in the pharmaceutical arts.

The dosage regimen utilizing the compounds of the present invention is selected in accordance with a variety of factors including type, species, age, weight, sex, and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches or iontophoretic devices well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms includes sodium oleate, sodium stearate, magnesium stearate, sodium benzoate, sodium acetate, sodium chloride, and the like. Disintegrators include without limitation starch, methylcellulose, agar, bentonite, xanthan gum, and the like.

The compounds of the present invention can also be administered in the form of liposome delivery systems, such as small unilamellar vesicles, large unilamellar vesicles and multilamellar vesicles. Liposomes can be formed from e. g. phospholipids, cholesterol, stearylamine, or phosphatidylcholines.

The following definitions apply to the terms as used throughout this specification, unless otherwise limited in specific instances.

The term "GR antagonist" as used herein is intended to cover any moiety that binds to a glucocorticoid receptor, or a complex of which a glucocorticoid receptor forms a part, and acts as an antagonist or a partial antagonist.

The term "halogen" and "halo", as used herein alone or as part of another group, refers to chlorine, bromine, fluorine, and iodine.

The term "heteroatom" and "hetero", as used herein, refers to nitrogen, oxygen, sulphur, and in heterocyclic rings, also selenium.

The term $C_{1-6}$-alkyl, as used herein alone or as part of another group, refers to an alkyl group which may be straight or branched. Exemplary $C_{1-6}$-alkyl groups include, but are not restricted to, methyl, ethyl, propyl, isopropyl, butyl, sec-butyl, tert-butyl, pentyl, isopentyl, hexyl, and isohexyl.

The term $C_{1-12}$-alkyl, as used herein alone or as part of another group, refers to an alkyl group which may be straight or branched. Exemplary $C_{1-12}$-alkyl groups include, but are not restricted to, methyl, ethyl, propyl, isopropyl, butyl, sec-butyl, tert-butyl, pentyl, isopentyl, neopentyl, hexyl, isohexyl, heptyl, octyl, isooctyl, nonyl, decyl, isodecyl, undecyl, and dodecyl.

The term $C_{3-8}$-cycloalkyl, as used herein alone or as part of another group, refers to a mono-, or bicyclic alkyl group, which may contain one or more unsaturations (double, and/or triple bonds). Exemplary $C_{3-8}$-cycloalkyl groups include, but are not restricted to, cyclopropyl, cyclobutyl, cyclopentyl, cyclohexyl, cycloheptyl, cyclooctyl, cyclopentenyl, cyclohexenyl, cycloheptenyl, cyclooctenyl, cyclooctynyl, bicycloheptyl, bicyclooctyl, and bicyclooctenyl. It is also understood that a single carbon of the $C_{3-8}$-cycloalkyl may be common to another $C_{3-8}$-cycloalkyl or $C_{3-8}$-heterocycloalkyl, forming a so called spiro-compound.

The term $C_{2-6}$-alkenyl, as used herein alone or as part of another group, refers to an alkenyl group which may be straight or branched. Exemplary $C_{2-6}$-alkenyl groups include, but are not restricted to, vinyl, 1-propenyl, 2-propenyl, propadienyl, 1-butenyl, 2-butenyl, 3-butenyl, 1,3-butadienyl, 1-pentenyl, 2-pentenyl, 4-pentenyl, and 5-hexenyl.

The term $C_{2-6}$-alkynyl, as used herein alone or as part of another group, refers to an alkynyl group which may be straight or branched. Exemplary $C_{2-6}$-alkynyl groups include, but are not restricted to, ethynyl, 1-propynyl, 2-propynyl, 1-butynyl, 2-butynyl, 3-butynyl, 1-pentynyl, 2-butynyl, 4-pentynyl, 1-hexynyl, 3-hexynyl, and 5-hexynyl.

The term $C_{3-8}$-heterocycloalkyl, as used herein alone or as part of another group, refers to a mono-, or bicyclic alkyl group which may contain one or more heteroatoms, and which may contain one or more unsaturations (double, and/or triple bonds). Exemplary $C_{3-8}$-heterocycloalkyl groups include, but are not restricted to, aziridine, azetidine, pyrrolidine, pyrroline, piperidine, tetrahydropyridine, dihydropyridine, pyrazolidine, imidazolidine, imidazoline, piperazine, morpholine, thiomorpholine, oxirane, oxetane, tetrahydrofuran, tetrahydropyran, dihydropyran, 1,3-dioxolan, 1,3-dioxane, 1,4-dioxane, thiirane, thietane, thiolane, 1,3-dithiolane, 1,4-dithiane, 1,3,5-trithiane, quinuclidine, and tropane. It is also understood that a single carbon or nitrogen of the $C_{3-8}$heterocycloalkyl may be common to another $C_{3-8}$-cycloalkyl-, or $C_{3-8}$-heterocycloalkyl-group, forming a so called spiro-compound.

The term aryl is intended to include monocyclic or bicyclic ring systems having from 6 to 10 ring carbon atoms, in which at least one ring is aromatic. Examples of such ring systems are benzene, naphtalene, 1,2,3,4-tetrahydronaphtalene, indan, and indene.

The term heteroaryl refers to a mono-, bi- or tricyclic ring system having from 5 to 10 ring atoms, in which at least one ring is aromatic, and in which one or more of the ring atoms are other than carbon, such as nitrogen, sulphur, oxygen and selenium. Examples of such heteroaryl rings include, but are not restricted to, pyrrole, furan, thiophene, pyrazole, imidazole, oxazole, isoxazole, thiazole, isothiazole, 1,2,3-triazole, 1,2,4-triazole, 1,3,4-triazole, 1,2,3-oxadiazole, 1,2,4-oxadiazole, 1,3,4oxadiazole, 1,2,3-thadiazole, 1,2,4-thiadiazole, 1,3,4-thiadiazole, tetrazole, pyridine, indole, isoindole, indoline, isoindoline, quinoline, 1,2,3,4-tetrahydroquinoline, isoquinoline, 1,2,3,4tetrahydroiso-quinoline, quinolizine, carbazole, acridine, benzofuran, isobenzofuran, chroman, isochroman, benzothiophene, pyridazine, pyrimidine, pyrazine, indazole, benzimidazole, cinnoline, quinazoline, quinoxaline, phthalazine, 1,5-naphthyridine, 1,8-naphthyridine, phenazine, benzoxazole, 3,4-dihydro-2H-1,4-benzoxazine, benzothiazole, phenothiazine, 1,3-benzodioxole, benzodioxane, 2,1,3-benzoxadiazole, 2,1,3-benzothiazole, 2,1,3-benzo-selenadiazole, purine, and pteridine. The ring system may be linked to the rest of the molecule via a carbon or nitrogen atom thereof.

The compounds of formula I in the invention may contain at least one chiral center and may therefore exist as optical isomers. The invention therefore comprises optically inactive racemic (rac) mixtures (a one to one mixture of enantiomers), optically enriched scalemic mixtures as well as optically pure individual enantiomers. The compounds in the invention also may contain more than one chiral center and therefore may exist as diastereomers. The invention therefore comprises individual diastereomers as well as any mixture of diastereomers.

The compound of formula I in the invention may contain geometrical isomers and may therefore exist as either the E (entgegen) or Z (zusammen) isomers. The invention therefore comprises individual E or Z isomers as well as any mixture of E and Z isomers.

The compound of formula I in the invention may exist in tautomeric forms, the invention therefore comprises the individual tautomeric forms as well as any mixture thereof.

The compounds of formula I can be present as salts, in particular pharmaceutically acceptable salts. If the compounds of formula I have, for example, at least one basic center, they can form acid addition salts. These are formed, for example, with inorganic acids, such as mineral acids, for example sulfuric acid, phosphoric acid or a hydrohalic acid, with organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $C_{1-6}$-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic group include monohydrochloride, hydrogensulfate, tartrate, fumarate or maleate.

Preferred salts of the compounds of formula I which include an acid group include sodium, potassium and magnesium salts and pharmaceutically acceptable organic aminos.

Also included within the scope of the invention are polymorphs, hydrates, and solvates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example in "Design of Prodrugs" ed. H. Bundgaard, Elsevier, 1985, which is incorporated by reference herein in its entirety.

The present invention includes within its scope metabolites of compounds of formula I. Metabolites of the compounds includes active species produced upon introduction of compounds of this invention into the biological milieu.

The present invention includes within its scope compounds of formula I in isotopically labelled form.

The compounds of formula I may be prepared by the exemplary processes described in the following reaction schemes. Exemplary reagents and procedures for these reactions appear hereinafter and in the working Examples.

Compounds of formula I of the invention may be prepared using the sequence of steps outlined in Schemes 1 to 5 set out below. The groups $R^1$, $R^2$, $R^3$, $R^4$, $R^5$, $R^6$, $R^7$, $R^8$, $R^9$, $R^{10}$, and $R^{11}$ in Schemes 1 to 5 are as defined in formula I. The groups $R^1$, $R^2$, $R^3$, $R^4$, $R^5$, $R^6$, $R^7$, $R^8$, $R^9$, $R^{10}$, and $R^{11}$ may be modified one or several times, after or during the preparation of compounds of formula I by methods known in the art. Examples of such methods include, but are not restricted to, substitutions, reductions, oxidations, alkylations, hydrolysis, esterifications and etherifications. E is $R^1$, or a group that can be transformed to $R^1$ in one or several synthetic steps after or during the preparation of compounds of formula I, by methods known by a person skilled in the art. Examples of such transformations include, but are not restricted to, nucleophilic substitutions of an alkyl group activated by a halogen or a sulphonic acid ester, hydrolysis of an ester or a nitrile to give a carboxylic add, or the transformation of a nitrile into a tetrazole.

Scheme 1 describes a synthetic route that begins with a coupling reaction between an appropriately substituted iodonium salt 2 and an appropriately substituted phenol 1 to give the diarylether 3. The coupling is preferably catalyzed by metals, preferably Cu, Ni, Pd, or suitable salts, complexes, oxides or hydroxides thereof in the presence of a base. Suitable bases include, but are not restricted to, triethylamine, pyridine, $K_2CO_3$ and $Cs_2CO_3$. Alternatives to this ether formation include, but is not restricted to, transition metal catalyzed couplings of phenols with aryl halides or arylboronic acids, or other reactions known by a person skilled in the art. In the next step compound 3 is converted to the ketone 4 by introducing $R^5CO$, e. g. by a Friedel-Crafts reaction of compound 3 with an appropriate acyl halid, carboxylic acid anhydrid, carboxylic acid, or ketene. The reaction is preferably performed in the presence of a Lewis or a Brønstedt acid. Suitable acids include, but are not restricted to, $H_2SO_4$, polyphosphoric acid, $CF_3SO_3H$, $TiCl_4$, $AlCl_3$, $ZnCl_2$, $BF_3.OEt_2$, and the like. Reduction of the ketone 4 by agents such as $NaBH_4$, $NaBH_3CN$, or diisobutylaluminium hydride may, dependent on the precise reaction conditions, yields the methylene compound 5($X=CH_2$) or the alcohol 6. Alternatively, the keto group in compound 4 may be trans-formed to an oxim (5, $X=C=NOR^8$) by a reaction with a suitable hydroxylamine, or to a thioketone (5, X=S) by e. g. a reaction with Lawesson's reagent, or with elemental sulfur in pyridine. The hydroxy group of compound 6 may be converted in one or several synthetic transformations to compound 7 where $X=CHR^7$ or where $X=CHYR^7$. Examples of such conversions include, but are not restricted to, synthetic transformations known to those skilled in the art, such as alkylations, arylations, acylations, halogenations, aminations and sulfurylations. If E is $R^1$ in compounds 4, 5, 6, or 7, the said compounds equals compounds of formula I of the present invention. If E is not $R^1$ in compounds 4, 5, 6, or 7, E is transformed to $R^1$ yielding compounds of formula I of the present invention. Such transformations may be performed in one or several synthetic steps and include, but are not restricted to, nucleophilic substitutions (e. g. by cyanides) of an alkyl group activated by a halogen or a sulphonic acid ester (e. g. by mesylate, tosylate or triflate), hydrolysis of esters or a nitrile to give a carboxylic acid, or the transformation of a nitrile into a tetrazole.

Scheme 1.

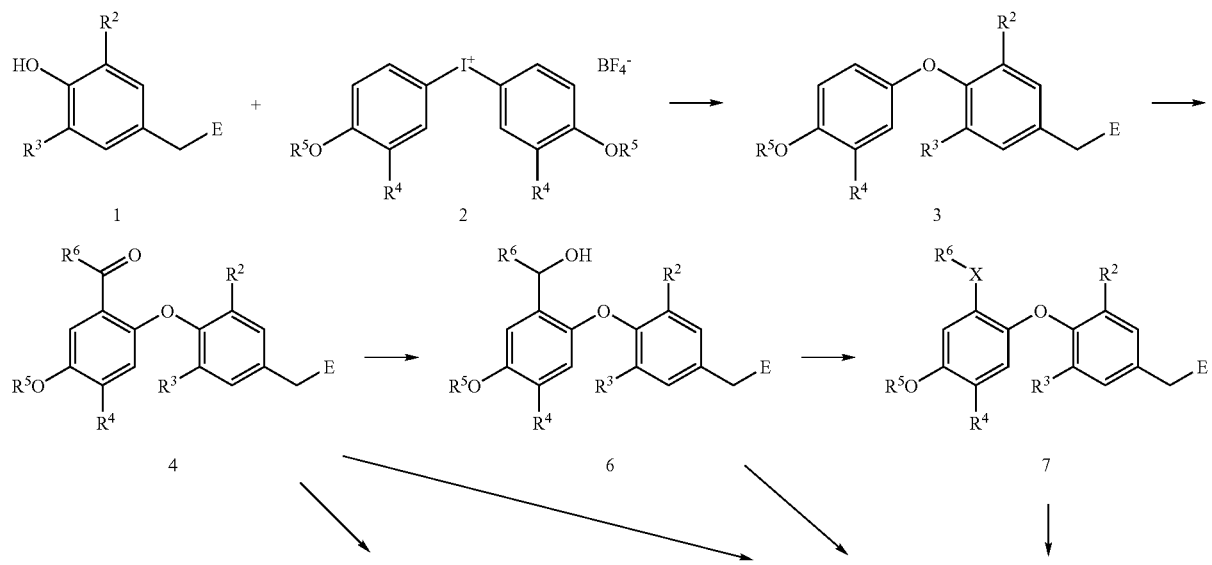

-continued

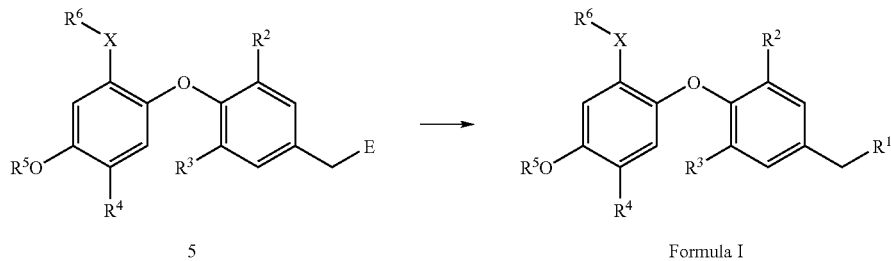

5 → Formula I

Scheme 2 describes an alternative synthesis to compound 3 in Scheme 1. As in Scheme 1, the synthetic route begins with a coupling reaction, in this case between the iodonium salt 8 and the phenol 1 to give the diarylether 9. The coupling is preferably catalyzed by metals, preferably Cu, Ni, Pd, or suitable salts, complexes, oxides or hydroxides thereof in the presence of a base. Suitable bases include, but are not restricted to, triethylamine, pyridine, $K_2CO_3$ and $Cs_2CO_3$. Alternatives to this ether formation include, but is not restricted to, transition metal catalyzed couplings of phenols with aryl halides or arylboronic acids, or other reactions known by a person skilled in the art. In the next step diarylether 9 is converted to the ketone 10 by introducing $R^4CO$, e. g. by a Friedel-Crafts reaction of diarylether 9 with an appropriate acyl halide, carboxylic acid anhydride, carboxylic acid, or ketene. The reaction is preferably performed in the presence of a Lewis or a Brønstedt acid. Suitable acids include, but are not restricted to, $H_2SO_4$, polyphosphoric acid, $CF_3SO_3H$, $TiCl_4$, $AlCl_3$, $ZnCl_2$, $BF_3.OEt_2$, and the like. Compound 10 is converted to compound 11 one or several synthetic steps by reactions including, but not restricted to, nucleophilic substitutions, reductions, olefinations, oxidations, alkylations, hydrolysis, esterifications and etherifications. When $R^A$, $R^B$ and $R^A$, together with the carbon to which they are bound equals $R^4$, compound 11 is the same as compound 3, that may be transformed to compounds of formula I of the present invention by using the synthetic sequences described in Scheme 1.

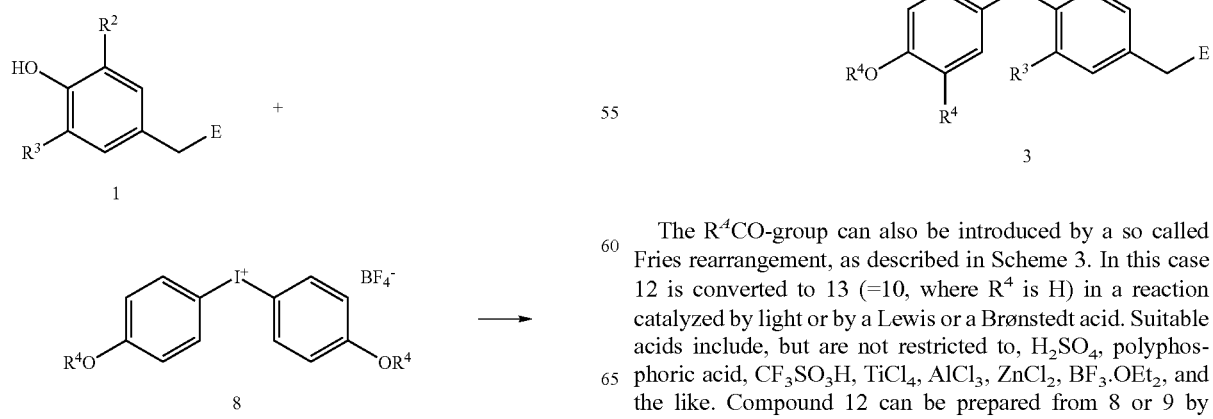

The $R^4CO$-group can also be introduced by a so called Fries rearrangement, as described in Scheme 3. In this case 12 is converted to 13 (=10, where $R^4$ is H) in a reaction catalyzed by light or by a Lewis or a Brønstedt acid. Suitable acids include, but are not restricted to, $H_2SO_4$, polyphosphoric acid, $CF_3SO_3H$, $TiCl_4$, $AlCl_3$, $ZnCl_2$, $BF_3.OEt_2$, and the like. Compound 12 can be prepared from 8 or 9 by synthetic transformations known to those skilled in the art.

Scheme 3.

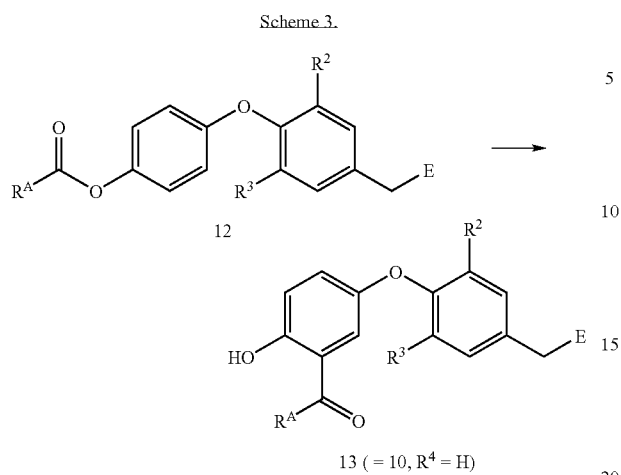

Scheme 4 describes yet another approach to introduce $R^4$ into the molecule. The diarylether 9 is halogenated to give compound 14 (W=halogen). Suitable halogenating agents include, but are not restricted to, iodine, NaI/NaOH, bromine, N-bromosuccinimide and 1,3-dibromo-5,5-dimethylhydantoin. Compound 14 is converted to compound 3 using one or several synthetic manipulations. Such synthetic manipulations include, but are not restricted to, transition metal catalyzed alkylations, alkenylations, alkynylations, and carbonylations. Scheme 4 also describes a sequence where the diarylether 9 is nitrated to give compound 14 (W=$NO_2$). The nitro group is then transformed in one or several synthetic steps, including, but not restricted to, reductions, diazotations, halogenations, cyanation and transition metal catalyzed reactions (as described above) to $R^4$ in compound 3.

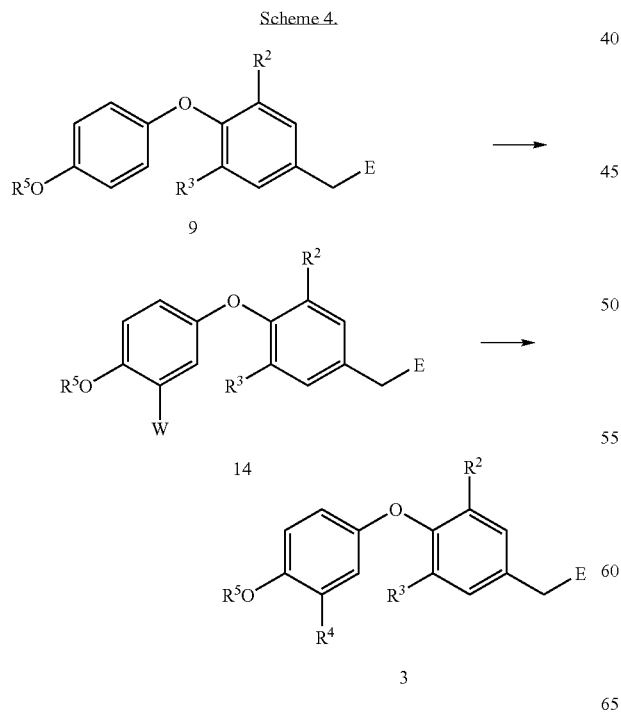

Scheme 5 depicts an alternative route to synthesize compound 6. The aldehyde group of 15 may be introduced into 3 by reactions including, but not restricted to, electrophilic substitution reactions. Suitable electrophilic substitution reactions include, but are not restricted to the Vilsmeier reaction (i. e. a combination of an activating agent such as $POCl_3$, $COCl_2$ or $(COCl)_2$ and an amide such as DMF or N-phenyl-N-methylformamide) or the combination of $MeOCHCl_2$ and $TiCl_4$. The $R^6$-group in 6 is introduced by a reaction of 14 with a nucleophile. Suitable nucleophiles include, but are not restricted to Grignard, organo-cerium, or organolithium reagents. Compound 6 may be transformed to compounds of formula I of the present invention by using the synthetic sequences described in Scheme 1.

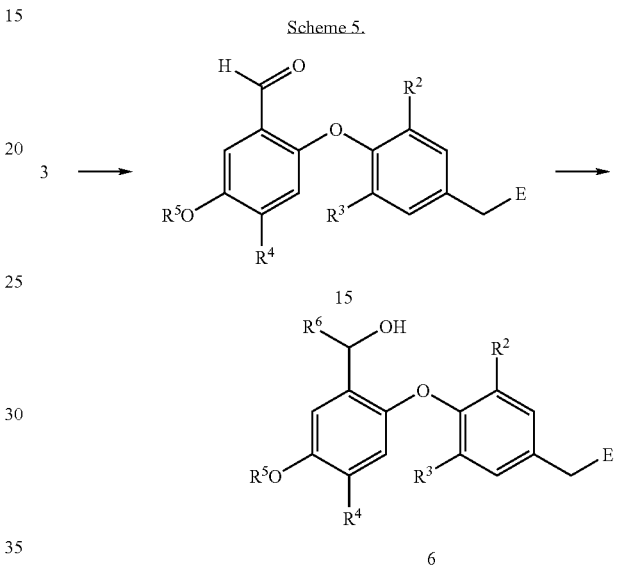

Those skilled in the art will readily understand that known variations of the processes described herein and of the experimental conditions, such as solvents, temperatures and times, of the following preparative procedures, can be used to prepare compounds of the formula I of the present invention.

The following working Examples represent preferred but non-limiting embodiments of the present invention.

EXAMPLE 1

3,5-Dibromo-4-[5-isopropyl-2-(3-methylbenzoyl)-4-(3-methyl-3-butenyloxy)-phenoxy]phenylacetic acid
(E1)

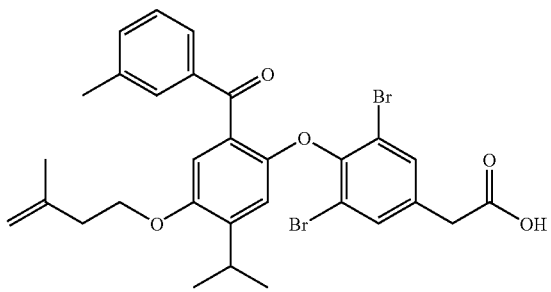

Step 1.

Bis(3-isopropyl-4-methoxyphenyl)iodonium tetrafluoroborate.

Fuming nitric acid (22.3 ml, 477 mmol) was added dropwise to 30.8 mL of acetic anhydride cooled in a dry ice/CCl$_4$ bath. Iodine (10.3 g, 40.6 mmol) was added in one portion followed by dropwise addition of trifluoroacetic acid (37.9 mL, 492 mmol). The mixture was stirred at room temperature until the iodine was dissolved and then purged with N$_2$ to remove nitrogen oxides. The mixture was concentrated, the residue dissolved in acetic anhydride (115 mL) and cooled in a dry ice/CCl$_4$ bath. A solution of 2-isopropylanisole (30 g, 200 mmol) in acetic anhydride (138 mL) and trifluoroacetic acid (20.5 mL) was added dropwise with stirring. The mixture was left at room temperature overnight and concentrated. The residue was taken up into MeOH (138 mL) and treated with 10% aqueous NaHSO$_3$ (138 mL) and 2M aqueous NaBF$_4$ (0.92 L). After the precipitate had aggregated, petroleum ether was added and the supernatant was decanted. The precipitate was triturated with petroleum ether, filtered, washed with petroleum ether and dried at room temperature under vacuum to afford 14.7 g (71%) of the title compound.

Step 2.

3,5-Dibromo-4-(3-isopropyl-4-methoxyphenoxy)phenylacetic acid methyl ester.

A solution of 3,5-dibromo-4-hydroxyphenylacetic acid methyl ester (5.27 g, 17.0 mmol) and triethylamine (1.89 g, 18.7 mmol) in CH$_2$Cl$_2$ (25 mL) was added dropwise to a mixture of bis(3-isopropyl-4-methoxyphenyl)iodonium tetrafluoroborate (13.0 g, 25.5 mmol) and copper bronze (2.14 g, 33.7 mmol) in CH$_2$Cl$_2$ (38 mL) at 0° C. The mixture was stirred in the dark for 4 d and filtered through celite. The filtrate was concentrated and the residue purified by chromatography on silica gel (petroleum ether/EtOAc, 98:2) to give 6.0 g (76%) of the title compound.

Step 3.

3,5-Dibromo-4-[5-isopropyl-4-methoxy-2-(3-methylbenzoyl)phenoxy]phenylacetic acid methyl ester.

TiCl$_4$ (25.2 mL, 229 mmol) was added dropwise to a solution of 3,5-dibromo-4-(3-isopropyl-4 -methoxyphenoxy)phenylacetic acid methyl ester (31.0 g, 65.6 mmol) and m-toluoyl-chloride (35.4 g, 229 mmol) in CH$_2$Cl$_2$ (310 mL) at 0° C. The mixture was stirred at room temperature for 3 d, cooled to 0 C, and quenched with ice (300 g). The layers were separated and the aqueous phase was extracted with EtOAc (3×100 mL). The combined organic phases were washed with NaHCO$_3$ (aq., sat, 3×100 mL), concentrated and purified by chromatography on silica gel to give 18.5 9 (49%) of the title compound.

Step 4.

3,5-Dibromo-4-[5-isopropyl-4-methoxy-2-(3-methylbenzoyl)phenoxy]phenylacetic acid.

3,5-Dibromo-4-[5-isopropyl-4-methoxy-2-(3-methylbenzoyl)phenoxy]phenylacetic acid methyl ester (2.5 g, 4 mmol) was dissolved in a 3:5 mixture of 1 M NaOH/MeOH (100 mL).

The mixture was stirred at room temperature for 17 h, acidified with 1 M HCl, concentrated to a small volume and extracted twice with EtOAc. The combined organic phases were dried over MgSO$_4$, concentrated and the residue dried under vacuum to give 1.9 g (80%) of a white solid. $^1$H NMR (CDCl$_3$): δ 7.80 (m, 2H), 7.42 (s, 2H), 7.33 (m, 2H), 6.98 (s, 1H), 6.24 (s, 1H), 3.80 (s, 3H), 3.57 (s, 2H), 3.22 (m, 1H), 2.37 (s, 3H), 1.07 (d, 6 H).

Step 5

3,5-Dibromo-4-[4-hydroxy-5-isopropyl-2-(3-methylbenzoyl)phenoxy]phenylacetic acid.

A 1M solution of BBr$_3$ in CH$_2$Cl$_2$ (12 mL, 12 mmol) was added slowly with a syringe to a stirred solution of 3,5-dibromo-4-[5-isopropylmethoxy-2-(3-methylbenzoyl)phenoxy]-phenylacetic acid (2 g, 3.5 mmol) in 20 mL CH$_2$Cl$_2$ at −20° C. After 15 min at −20° C. the solution was allowed to reach room temperature. After an additional 1 h at room temperature, the solution was poured onto ice and extracted three times with EtOAc. The combined extracts were dried over MgSO$_4$ and concentrated to give the title compound which was used in the next step without further purification. $^1$H NMR (CDCl$_3$): δ 7.8–7.7 (m, 2H), 7.5 (s, 2H), 7.4–7.3 (m, 2H), 6.9 (s, 1H), 6.2 (s, 1H), 3.6 (s, 2H), 3.3–3.2 (m, 1H), 2.4 (s, 3H), 1.1 (d, 6H).

Step 6

3,5-Dibromo-4-[4hydroxy-5-isopropyl-2-(3-methylbenzoyl)phenoxy]phenylacetic acid methyl ester.

Five drops of SOCl$_2$ was added to a solution of 3,5-dibromo-4-[4-hydroxy-5-isopropyl-2 -(3-methylbenzoyl) phenoxy]phenylacetic acid (0.30 g, 0.52 mmol), in 20 mL MeOH. The mixture was stirred at room temperature for 12 h and concentrated leaving the title compound (0.18 g, 60%). $^1$H NMR (CDCl$_3$): δ 7.9–7.7 (m, 2H), 7.5–7.1 (m, 4H), 6.9 (s, 1H), 6.2 (s, 1H), 4.7 (s, 3H), 4.5 (s, 2H), 3.1 (m, 1H), 2.4 (s, 3H), 1.1 (d, 6H).

Step 7

3,5-Dibromo-4-[5-isopropyl-2-(3methylbenzoyl)-4-(3-methyl-3-butenyloxy)phenoxy]phenyl-acetic acid.

A solution of diethyl azodicarboxylate (42 mg, 0.24 mmol) in anhydrous CH$_2$Cl$_2$ (1 mL) was added over 15 min to an ice-cooled, stirred mixture of 3,5-dibromo-4-[4-hydroxy-5-isopropyl-2-(3-methylbenzoyl)phenoxy]phenylacetic acid methyl ester (70 mg, 0.12 mmol), PPh$_3$ (63 mg, 0.24 mmol) and 3-methyl-3-buten-1-ol (24 µL, 0.24 mmol) in anhydrous CH$_2$Cl$_2$ (2 mL). The mixture was stirred at 0° C. for 12 h and 3 d at room temperature, and concentrated. The residue was dissolved in 30% NaOH/MeOH (2 mL) and heated at 40° C. for 12 h. The solution was allowed to cool, acidified with 1M HCl, concentrated and purified by HPLC to give the title compound. $^1$H NMR (CDCl$_3$): δ 7.9–7.7 (m, 2H), 7.5 (s, 2H), 7.4–7.3 (m, 2H), 7.0 (s, 1H), 6.3 (s, 1H), 4.8 (d, 2H), 4.1 (t, 2H), 3.6 (s, 2H), 3.3–3.2 (m, 1H), 2.5 (t, 2H), 2.4 (s, 3H), 1.8 (s, 3H), 1.1 (d, 6H). ESMS: m/z 629 (M−1).

The title compounds of Examples 2–29 were obtained as in Example 1 using the appropriate alcohols.

EXAMPLE 2

3,5-Dibromo-4-[5-isopropyl-2-(3-methylbenzoyl)-4-(2-propynyloxy)-phenoxy]phenylacetic acid (E2)

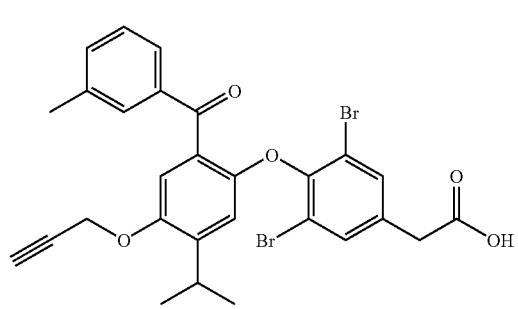

¹H NMR (CDCl₃): δ 7.9–7.7 (m, 2H), 7.5 (s, 2H), 7.4–7.3 (m, 2H), 7.1 (s, 1H), 6.3 (s, 1H), 4.7(d, 2H), 3.6 (s, 2H), 3.3–3.2 (m, 1H), 2.5 (t, 1H), 2.4 (s, 3H), 1.1 (d, 6H). ESMS: m/z 599 (M−1).

EXAMPLE 3

3,5-Dibromo-4-[5-isopropyl-2-(3-methylbenzoyl)-4-(pent-3-ynyloxy)phenoxy]-phenylacetic acid (E3)

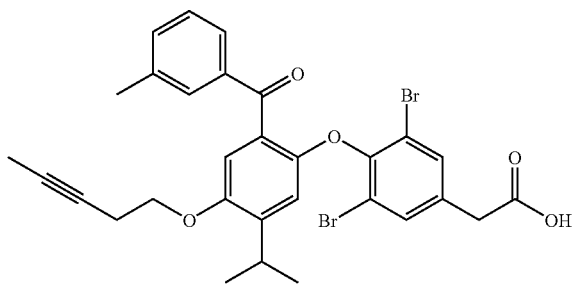

¹H NMR (CDCl₃): δ 7.9–7.8 (m, 2H), 7.7–7.2 (m, 4H), 7.0 (s, 1H), 6.2 (s, 1H), 4.0 (t, 2H), 3.6 (s, 2H), 3.3–3.2 (m, 1H), 2.7–2.5 (m, 2H), 2.4 (s, 3H), 1.8 (m, 3H), 1.1 (d, 6H). ESMS: m/z 627 (M−1).

EXAMPLE 4

3,5-Dibromo-4-[4(2-methoxyethoxy)-5-isopropyl-2-(3-methylbenzoyl)phenoxy]-phenylacetic acid (E4)

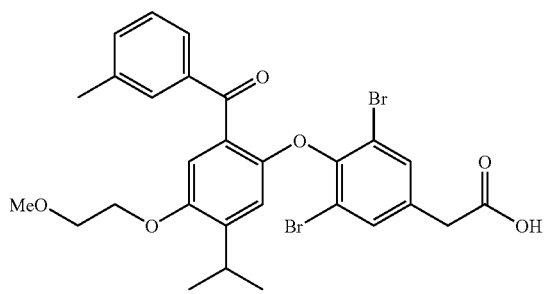

¹H NMR (CDCl₃): δ 7.9–7.7 (m, 2H), 7.5 (s, 2H), 7.4–7.3 (m, 2H), 7.0 (s, 1H), 6.2 (s, 1H), 4.1 (t, 2H), 3.8 (t, 2H), 3.6 (s, 2H), 3.4 (s, 3H), 3.3–3.2 (m, 1H), 2.4 (s, 3 H), 1.1 (d, 6H). ESMS: m/z 619 (M−1).

EXAMPLE 5

3,5-Dibromo-4-[4-(2-{2-methoxyethoxy}ethoxy)-5-isopropyl-2-(3-methylbenzoyl)-phenoxy]phenylacetic acid (E5)

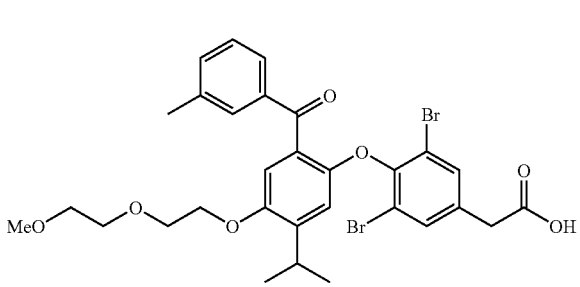

¹H NMR (CDCl₃): δ 7.9–7.7 (m, 2H), 7.5 (s, 2H), 7.4–7.3 (m, 2H), 7.0 (s, 1H), 6.2 (s, 1H), 4.1 (t, 2H), 3.9 (t, 2H), 3.7 (m, 2H), 3.6–3.5 (m, 5H), 3.4 (s, 2H), 3.3–3.2 (m, 1H), 2.4 (s, 3H), 1.1 (d, 6H). ESMS: m/z 663 (M−1).

EXAMPLE 6

3,5-Dibromo-4-[4-(2-{2-[2-methoxyethoxy]ethoxy)}ethoxyl-5-isopropyl-2-(3-methylbenzoyl)-phenoxy]phenylacetic acid (E6)

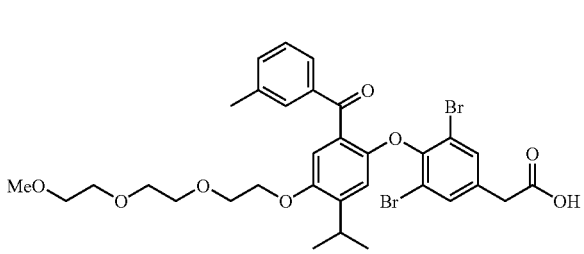

¹H NMR (CDCl₃): δ 7.9–7.8 (m, 2H), 7.5 (s, 2H), 7.47.3 (m, 2H), 7.0 (s, 1H), 6.2 (s, 1H), 4.1 (t, 2H), 3.9 (t, 2H), 3.7–3.5 (m, 11H), 3.4 (s, 2H), 3.3–3.2 (m, 1H), 2.4 (s, 3H), 1.1 (d, 6H). ESMS: m/z 707 (M−1).

EXAMPLE 7

3,5-Dibromo-4-[4-(7-hydroxyheptyloxy)-5-isopropyl-2-(3-methylbenzoyl)-phenoxy]phenylacetic acid (E7)

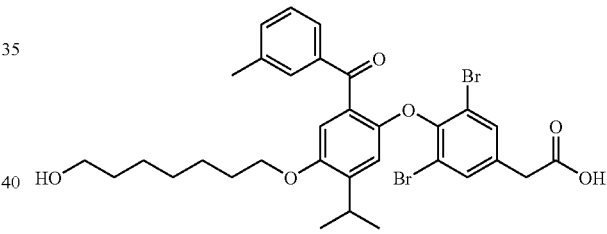

¹H NMR (CDCl₃): δ 7.8 (m, 2H), 7.5–7.3 (m, 4H), 7.0 (s, 1H), 6.3 (s, 1H), 4.0 (t, 2H), 3.7–3.5 (m, 4H), 3.3–3.2 (m, 1H), 2.4 (s, 3H), 1.9–1.7 (m, 2H), 1.6–1.3 (m, 8H), 1.1 (d, 6H). ESMS: m/z 675 (M−1).

EXAMPLE 8

3,5-Dibromo-4-[4-(2-ethylthioethoxy)-5-isopropyl-2-(3-methylbenzoyl)phenoxy]-phenylacetic acid (E8)

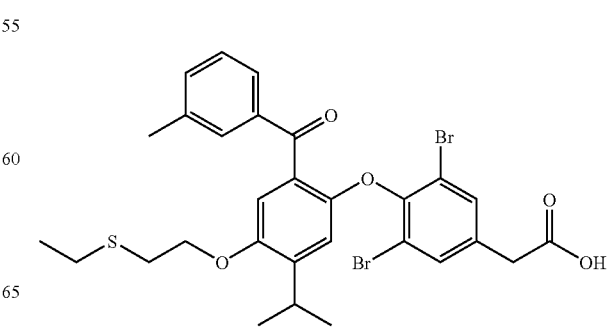

¹H NMR (CDCl₃): δ7.8–7.7 (m, 2H), 7.5 (s, 2H), 7.4–7.3 (m, 2H), 7.0 (s, 1H), 6.3 (S, 1H), 4.0 (t, 2H), 3.6 (s, 2H), 3.3–3.2 (m, 1H), 2.9 (t, 2H), 2.7–2.5 (m, 2H), 2.4 (s, 3H), 1.3 (t, 3H), 1.1 (d, 6H). ESMS: m/z 649 (M−1).

EXAMPLE 9

3,5-Dibromo-4-[4-carboxymethoxy-5-isopropyl-2-(3-methylbenzoyl)-phenoxy]phenylacetic acid (E9)

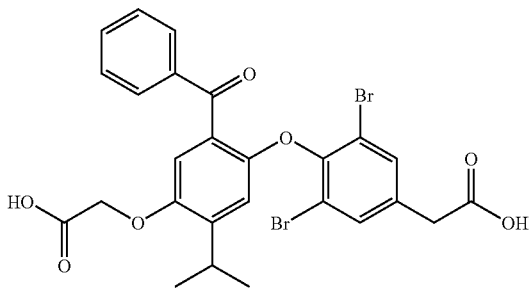

¹H NMR (DMSO-d₆): δ 7.80–7.55 (m, 4H), 7.50–7.35 (m, 2H), 6.83 (s, 1H), 6.15 (s, 1H), 4.26 (s, 2H), 3.52 (s, 2H), 3.35–3.15 (m, 1H), 2.35 (s, 3H), 1.03 (d, 6H). ESMS: m/z 605 (M−1).

EXAMPLE 10

3,5-Dibromo-4-[4-(5-carboxypentoxy)-5-isopropyl-2-(3-methylbenzoyl)-phenoxy]phenylacetic acid (E10)

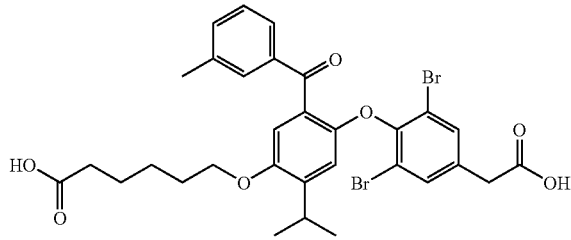

¹H NMR (CDCl₃): δ 7.9–7.8 (m, 2H), 7.5 (s, 2H), 7.4–7.3 (m, 2H), 7.0 (s, 1H), 6.2 (s, 1H), 4.0 (t, 2H), 3.6 (s, 2H), 3.3–3.2 (m, 1H), 2.4–2.3 (m, 3H), 1.8–1.4 (m, 8H), 1.0 (d, 6H). ESMS: m/z 657 (M−1).

EXAMPLE 11

3,5-Dibromo-4-[4-benzyloxy-5-isopropyl-2-(3-methylbenzoyl)phenoxy]phenylacetic acid (E11)

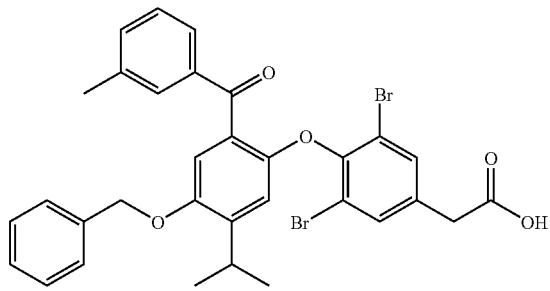

¹H NMR (CDCl₃): δ 7.9–7.7 (m, 2H), 7.5–7.2 (m, 9H), 7.1 (s, 1H), 6.3 (s, 1H), 5.1 (s, 2H), 3.6 (s, 2H), 3.3–3.2 (m, 1H), 2.4 (s, 3H), 1.1 (d, 6H). ESMS: m/z 651 (M−1).

EXAMPLE 12

3,5-Dibromo-4-[4-(2-fluorobenzyloxy)-5-isopropyl-2-(3-methylbenzoyl)-phenoxy]phenylacetic acid (E12)

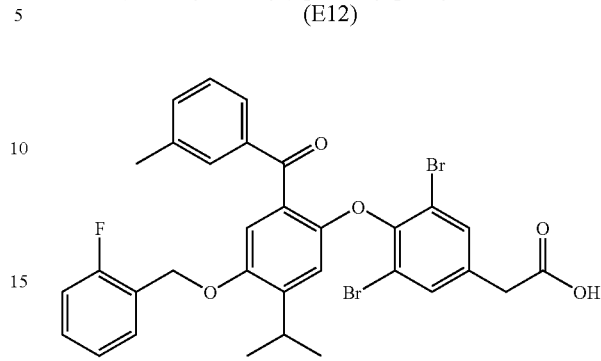

¹H NMR (CDCl₃): δ 7.9–7.8 (m, 2H), 7.6–7.0 (m, 9H), 6.3 (s, 1H), 5.1 (d, 2H), 3.6 (s, 2H), 3.3–3.2 (m, 1H), 2.4 (s, 3H), 1.1 (d, 6H). ESMS: m/z 669 (M−1).

EXAMPLE 13

3,5-Dibromo-4-[4-(3-fluorobenzyloxy)-5-isopropyl-2-(3-methylbenzoyl-phenoxy]phenylacetic acid (E13)

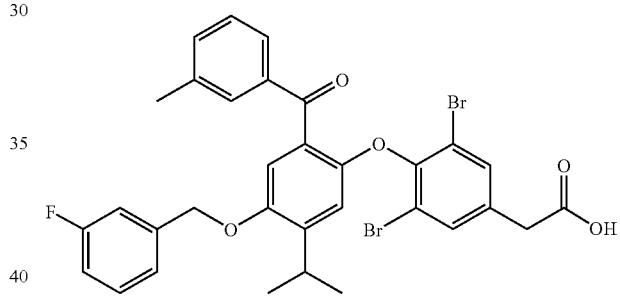

¹H NMR (CDCl₃): δ 7.9–7.8 (m, 2H), 7.6–7.0 (m, 9H), 6.3 (s, 1H), 5.1 (d, 2H), 3.6 (s, 2H), 3.3–3.2 (m, 1H), 2.4 (s, 3H), 1.1(d, 6H). ESMS: m/z 669 (M−1).

EXAMPLE 14

3,5-Dibromo-4-[4-(4-fluorobenzyloxy)-5-isopropyl-2-(3-methylbenzoyl)-phenoxy]phenylacetic acid (E14)

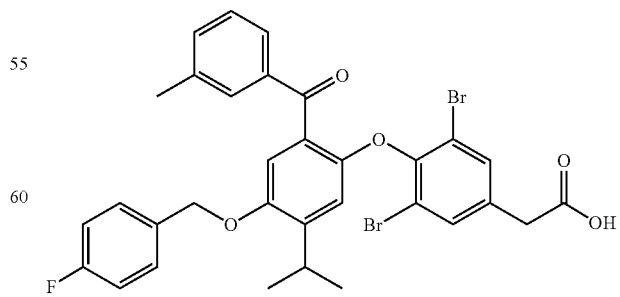

¹H NMR (CDCl₃): δ 7.9–7.8 (m, 2H), 7.6–7.0 (m, 9H), 6.3 (s, 1H), 5.1 (d, 2H), 3.6 (s, 2H), 3.3–3.2 (m, 1H), 2.4 (s, 3H), 1.1 (d, 6H). ESMS: m/z 669 (M−1).

EXAMPLE 15

3,5-Dibromo-4-[5-isopropyl-2-(3-methylbenzoyl)-4-(3-methylbenzyloxy)-phenoxy]phenylacetic acid (E15)

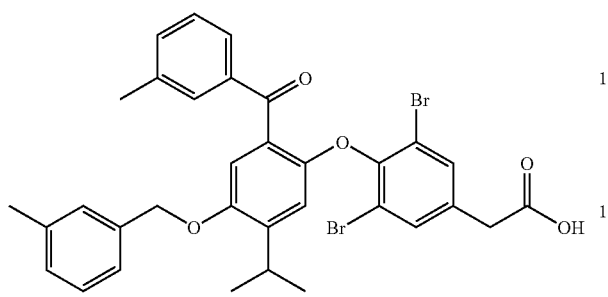

¹H NMR (CDCl₃): δ 7.9–7.7 (m, 2H), 7.5–7.0 (m, 9H), 6.3 (s, 1H), 5.0 (s, 2H), 3.6 (s, 2H), 3.3–3.2 (m, 1H), 2.4 (d, 6H), 1.1 (d, 6H). ESMS: m/z 665 (M1).

EXAMPLE 16

3,5-Dibromo-4-[4-(4-tert-butoxybenzyl)-5-isopropyl-2-(3-methylbenzoyl)-phenoxy]phenylacetic acid (E16)

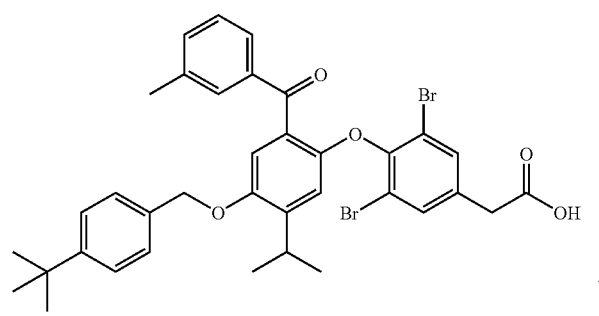

¹HNMR (CDCl₃): δ 7.9–7.8 (m, 2H), 7.6–7.2 (m, 8H), 7.1 (s, 1H), 6.3 (s, 1H), 5.1 (s, 2H), 3.6 (s, 2H), 3.4–3.3 (m, 1H), 2.4 (s, 3H), 1.3 (s, 9H), 1.1 (d, 6H). ESMS m/z 707 (M−1).

EXAMPLE 17

3,5-Dibromo-4-[5-isopropyl-2-(3-methylbenzoyl-4-(4-trifluoromethoxy-benzyloxy)phenoxy]phenylacetic acid (E17)

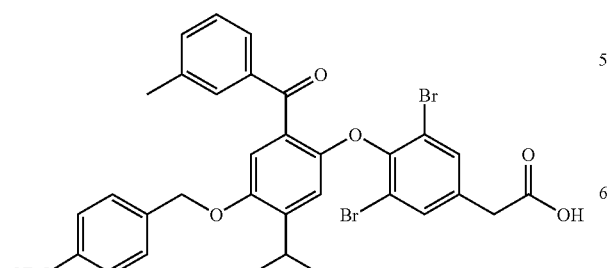

¹H NMR (CDCl₃): δ 7.9–7.8 (m, 2H), 7.6–7.0 (m, 9H), 6.3 (s, 1H), 5.1 (s, 2H), 3.6 (s, 2H), 3.3–3.3 (m, 1H), 2.4 (s, 3H), 1.1 (d, 6H). ESMS: m/z 735 (M−1).

EXAMPLE 18

3,5-Dibromo-4-[5-isopropyl-2-(3-methylbenzoyl)-4-(3-nitrobenzyloxy)-phenoxy]phenylacetic acid (E18)

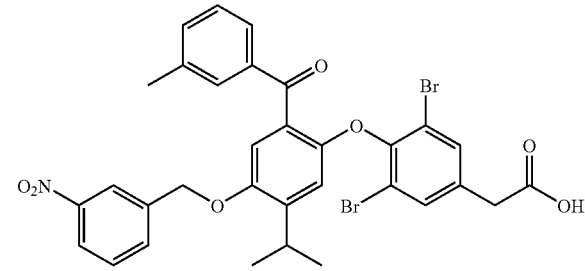

¹H NMR (CDCl₃): δ7.9–7.7 (m, 3H), 7.6–7.2 (m, 7H), 7.1 (s, 1H), 6.3 (s, 1H), 5.1 (s, 2H), 3.6 (s, 2H), 3.4–3.3 (m, 1H), 2.4 (s, 3H), 1.1 (d, 6H). ESMS: m/z 696 (M−1).

EXAMPLE 19

3,5-Dibromo-4-[4-(4-carboxybenzyloxy)-5-isopropyl-2-(3-methylbenzoyl-phenoxy]phenylacetic acid (E19)

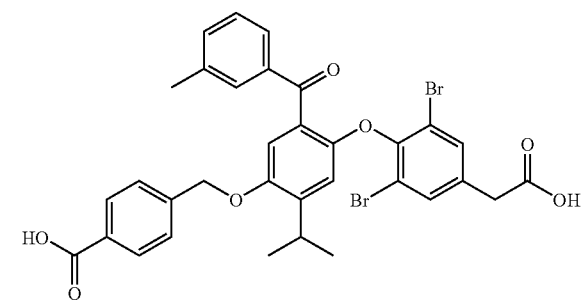

¹H NMR (CDCl₃): δ 8.1 (d, 2H), 7.9–7.8 (m, 2H), 7.6–7.4 (m, 4H), 7.3–7.2 (m 2H), 7.0 (s, 1H), 6.3 (s, 1H), 5.1 (s, 2H), 3.6 (s, 2H), 3.4–3.3 (m, 1H), 2.4 (s, 3H), 1.1 (d, 6H). ESMS: m/z 695 (M−1).

EXAMPLE 20

3,5-Dibromo-4-[4-(4-carbomethoxybenzyloxy)-5-isopropyl-2-(3-methylbenzoyl)-phenoxy]phenylacetic acid (E20)

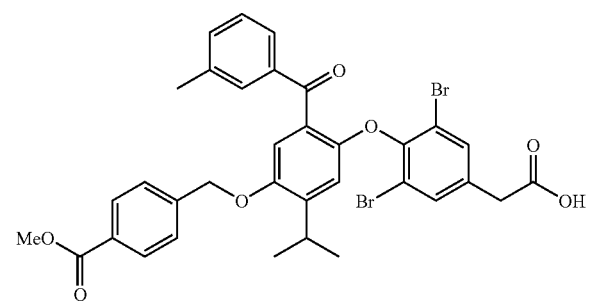

¹H NMR (CDCl₃): δ 8.1 (d, 2H), 7.9–7.8 (m, 2H), 7.5–7.4 (m, 4H), 7.4–7.2 (m, 2H), 7.1 (s, 1H), 6.3 (s, 1H), 5.1 (s, 2H), 3.9 (s, 3H), 3.6 (s, 2H), 3.4–3.3 (m, 1H), 2.4 (s, 3H), 1.1 (d, 6H). ESMS: m/z 709 (M−1)

EXAMPLE 21

3,5-Dibromo-4-[4-(3,5-difluorobenzyloxy)-5-isopropyl-2-(3-methylbenzoyl)-phenoxy]phenylacetic acid (E21)

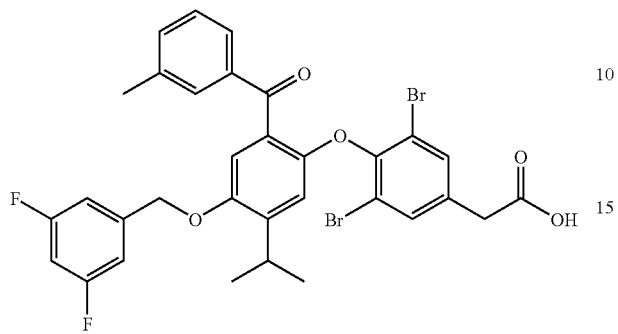

$^1$H NMR (CDCl$_3$): δ 7.9–7.7 (m, 2H), 7.6–7.2 (m, 5H), 7.1–6.9 (m, 2H), 6.8–6.6 (m, 1H), 6.3 (s, 1H), 5.1 (s, 2H), 3.6 (s, 2H), 3.3–3.2 (m, 1H), 2.4 (s, 3H), 1.1 (d, 6H). ESMS: m/z 687 (M−1).

EXAMPLE 22

3,5-Dibromo-4-[4-(4-bromo-2-methoxybenzyloxy)-5-isopropyl-2-(3-methylbenzoyl)-phenoxy]phenylacetic acid (E22)

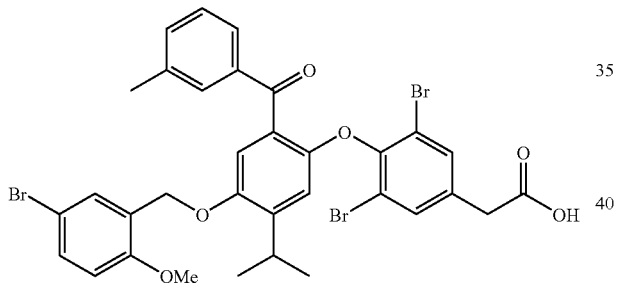

$^1$H NMR (CDCl$_3$): δ 7.9–7.7 (m, 2H), 7.6–7.2 (m, 6H), 7.1 (s, 1H), 6.7 (d, 1H), 6.3 (s, 1H), 5.1 (s, 2H), 3.8 (s, 3H), 3.6 (s, 2H), 3.3–3.2 (m, 1H), 2.4 (s, 3H), 1.1 (d, 6H). ESMS: m/z 760 (M−1).

EXAMPLE 23

3,5-Dibromo-4-[4-(2-chloro-4,5-{methylenedioxy}benzyloxy)-5-isopropyl-2-(3-methylbenzoyl)phenoxy]phenylacetic acid (E23)

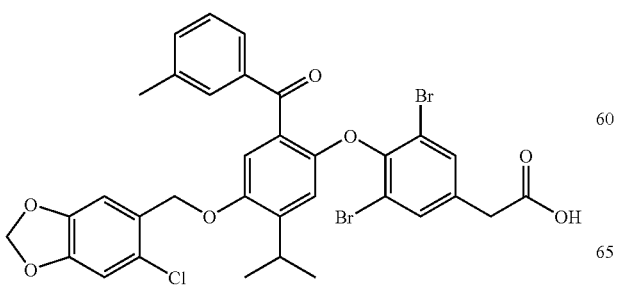

$^1$H NMR (CDCl$_3$): δ 7.9–7.8 (m, 2H), 7.5–7.2 (m, 4H), 7.1 (s, 1H), 7.0 (s, 1H), 6.9 (s, 1H), 6.3 (s, 1H), 6.0 (s, 2H), 5.0 (s, 2H), 3.6 (s, 2H), 3.4–3.3 (m, 1H), 2.4 (s, 3H), 1.1 (d, 6H). ESMS: m/z 730 (M−1).

EXAMPLE 24

3,5-Dibromo-4-[5-isopropyl-2-(3-methylbenzoyl)-4-(4-pyridinylmethoxy)-phenoxy]phenylacetic acid (E24)

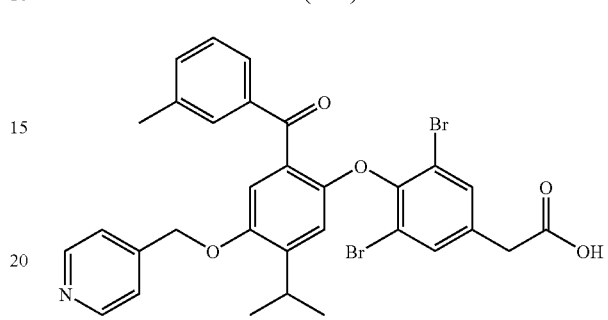

$^1$H NMR (CDCl$_3$): δ 7.9–7.7 (m, 2H), 7.5–7.2 (m, 8H), 7.1 (s, 1H), 6.2 (s, 1H), 5.1 (s, 2H), 3.6 (s, 2H), 3.3–3.2 (m, 1H), 2.4 (s, 3H), 1.1 (d, 6H). ESMS: m/z 652 (M1).

EXAMPLE 25

3,5-Dibromo-4-[5-isopropyl-2-(3-methylbenzoyl)-4-(2-{4-methyl-5-thiazolyl}-ethoxy)phenoxy]phenylacetic acid (E25)

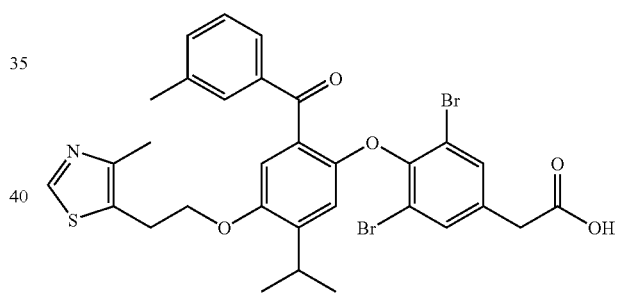

$^1$H NMR (CDCl$_3$): δ 8.6 (s, 1H), 7.9–7.8 (m, 2H), 7.5 (s, 2H), 7.4–7.3 (m, 2H), 7.0 (s, 1H), 6.2 (s, 1H), 4.1 (t, 2H), 3.6 (s, 2H), 3.3–3.2 (m, 3H), 2.5 (s, 3H), 2.4 (s, 3H), 1.0 (s, 6H). ESMS: m/z 686 (M−1).

EXAMPLE 26

3,5-Dibromo-4-[5-isopropyl-2-(3-methylbenzoyl)-4-(3-phenyl-2-propenyloxy)-phenoxy]phenylacetic acid (E26)

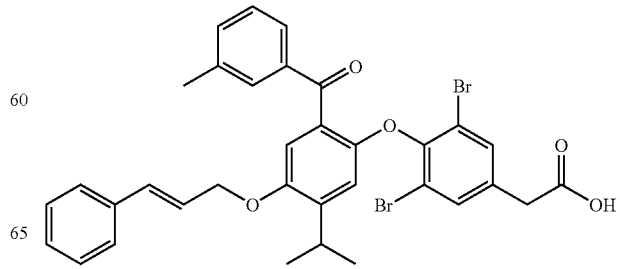

$^1$H NMR (CDCl$_3$): δ 7.9–7.8 (m, 2H), 7.5–7.2 (m, 9H), 7.1 (s, 1H), 6.7 (d, 1H), 6.5–6.3 (m, 1H), 6.2 (s, 1H), 4.7 (d, 2H), 3.6 (s, 2H), 3.3–3.2 (m, 1H), 2.4 (s, 3H), 1.1 (d, 6H). ESMS: m/z 677 (M−1).

EXAMPLE 27

3,5-Dibromo-4-[5-isopropyl-2-(3-methylbenzoyl)-4-(4-phenylbutyloxy)phenoxy]-phenylacetic acid (E27)

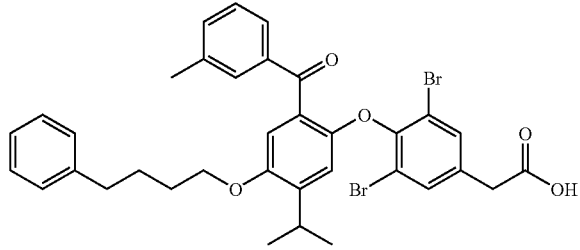

$^1$H NMR (CDCl$_3$): δ 7.9–7.7 (m, 2H), 7.5–7.1 (m, 9H), 7.0 (s, 1H), 6.2 (s, 1H), 4.0 (m, 2H), 3.6 (s, 2H), 3.3–3.2 (m, 1H), 2.8–2.6 (m, 2H), 2.4 (s, 3H), 1.9–1.7 (m, 4H), 1.1 (d, 6H). ESMS: m/z 693 (M−1).

EXAMPLE 28

3,5-Dibromo-4-[5-isopropyl-2-(3-methylbenzoyl)-4-(2-{N-piperidino}ethoxy)-phenoxy]phenylacetic acid (E28)

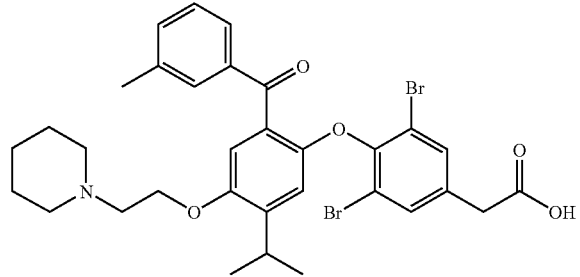

$^1$H NMR (CDCl$_3$): δ 7.9–7.7 (m, 2H), 7.5 (s, 2H), 7.4–7.3 (m, 2H), 7.0 (s, 1H), 6.3 (s, 1H), 4.3–4.2 (m, 2H), 3.5 (s, 2H), 3.2 (m, 3H), 3.0 (m, 4H), 2.4 (s, 3H), 1.8 (m, 4H), 1.5–1.3 (m, 2H), 1.1 (d, 6H). ESMS: m/z 672 (M−1).

EXAMPLE 29

3,5-Dibromo-4-[5-isopropyl-2-(3-methylbenzoyl)-4-(2-{N-morpholino}ethoxy)-phenoxy]phenylacetic acid (E29)

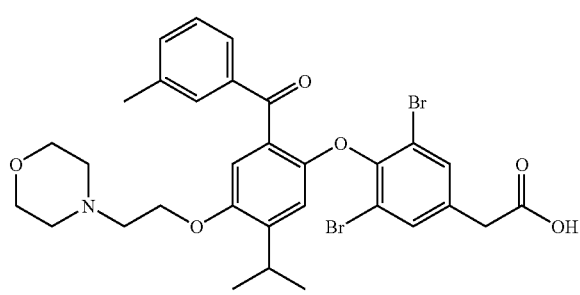

$^1$H NMR (CDCl$_3$): δ 7.9–7.7 (m, 2H), 7.5 (s, 2H), 7.4–7.3 (m, 2H), 7.0 (s, 1H), 6.3 (s, 1H), 4.2 (m, 2H), 3.7 (m, 2H), 3.6 (m, 2H), 3.5 (s, 2H), 3.2 (m, 3H), 3.0 (m, 4H), 2.4 (s, 3H), 1.1 (d, 6H). ESMS: m/z 674 (M−1).

The compounds of the present invention according to the general formula I exhibits an affinity for the glucocorticoid receptor in the range between 0.1 and 5000 nM.

The invention claimed is:

1. A compound according to the formula I:

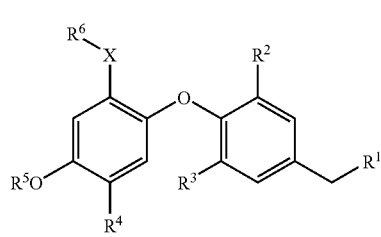

wherein:

X is selected from:

C=O, or C=S;

Y is selected from:

O, S, and NR$^8$;

R$^1$ is COOH;

R$^2$ and R$^3$ are independently of each other selected from: hydrogen, halogen, and C$_{1-6}$-alkyl, provided that one of R$^2$ or R$^3$ is other than hydrogen;

R$^4$ is (i) C$_{1-6}$-alkyl, C$_{2-6}$-alkenyl and C$_{2-6}$-alkynyl, wherein any residues herein may be optionally substituted in one or more positions independently of each other by a group selected from A;

R$^5$ is selected from:

(iii) C$_{1-6}$-alkyl which is substituted by a group selected from A, provided that A is not halogen;

(iv) C$_{7-12}$-alkyl, C$_{2-12}$-alkenyl and C$_{2-12}$-alkynyl, wherein any residues herein may be optionally substituted in one or more positions independently of each other by a group selected from A;

(v) C$_{1-12}$-alkyl, where one or more carbon atoms are independently of each other replaced by a group selected from Y, and where one or more carbons are optionally substituted by a group selected from A, provided that if more than one carbon is replaced by Y, the said Y groups are not directly connected to each other;

R$^6$ is (vii) aryl and heteroaryl, wherein any residues herein may be optionally substituted in one or more positions independently of each other by a group selected from C;

R$^8$, R$^9$, R$^{10}$ and R$^{11}$ are independently of each other selected from:

(viii) hydrogen, (ix) C$_{1-6}$-alkyl, C$_{3-8}$-cycloalkyl, C$_{2-6}$-alkenyl, C$_{2-6}$-alkynyl, and C$_{3-8}$-heterocycloalkyl, wherein any residues herein may be optionally substituted in one or more positions independently of each other by a group selected from A;

(x) aryl and heteroaryl, wherein any residues herein may be optionally substituted in one or more positions independently of each other by a group selected from C;

or where any pair of $R^8$, $R^9$, $R^{10}$ and $R^{11}$ together with the atom or atoms to which they are bound form a ring having 3–7 ring members, and which ring optionally contain 1–3 heteroatoms, or 1–3 double bonds, and which optionally is substituted by a group selected from A;

A is selected from:

halogen, $C_{3-8}$-cycloalkyl, $C_{2-8}$-alkenyl, $C_{2-6}$-alkynyl, aryl, $C_{3-8}$-heterocycloalkyl, heteroaryl, cyano, nitro, azido, Z, $R^8O$, $R^8C(Z)$, $R^8C(Z)O$, $R^8OC(Z)$, $R^8S$, $R^8S(O)_n$, $R^8S(O)_nO$, $R^8OS(O)_m$, $(R^9)(R^{10})N$, $(R^9)(R^{10})NC(Z)$, $(R^9)(R^{10})NC(Z)O$, $R^8C(Z)N(R^{11})$, $(R^9)(R^{10})NC(Z)N(R^{11})$, $(R^9)(R^{10})NS(O)_2$, $R^8S(O)_2N(R^{11})$, $(R^9)(R^{10})NS(O)_2N(R^{11})$, and $R^8SC(Z)N(R^{11})$, wherein any $C_{1-6}$-alkyl, $C_{3-8}$-cycloalkyl, $C_{2-6}$-alkenyl, $C_{2-6}$-alkynyl, and $C_{3-8}$-heterocycloalkyl residue is optionally substituted in one or more positions independently of each other by a group selected from B, and also wherein any aryl and heteroaryl residue is optionally substituted in one or more positions independently of each other by a group selected from C; provided that if A is attached to a double or to a triple bond, or to a carbon attached to a heteroatom, A is not HO, HS, $R^9HN$, $(R^9)(R^{10})NC(Z)NH$, $(R^9)(R^{10})NS(O)_2NH$, or $R^8S(O)_2NH$, and also provided that if A is attached to a double or to a triple bond, A is not Z;

B is defined as:

A, provided that if B is attached to a double or to a triple bond, or to a carbon attached to a heteroatom, B is not HO, HS, $R^9HN$, $(R^9)(R^{10})NC(Z)NH$, $(R^9)(R^{10})NS(O)_2NH$, or $R^8S(O)_2NH$, and also provided that if B is attached to a double or to a triple bond, B is not Z;

C is defined as:

A, provided that C is not Z;

Z is a substituent connected by a double bond, and is selected from:

O=, S=, $R^8N$=, $(R^9)(R^{10})NN$=, $R^8ON$=, $(R^9)(R^{10})NS(O)_2N$=, NCN=, $O_2NCH$=, and $(R^9)(R^{10})C$=;

n is 1 or 2;

or pharmaceutically acceptable salts, stereoisomers or prodrugs thereof.

2. A compound according to claim 1 wherein wherein X is C=O.

3. A compound according to any one of claim 1, wherein $R^2$ and $R^3$ are independently of each other, halogen or $C_{1-6}$-alkyl.

4. A compound according to claim 3 wherein both $R^2$ and $R^3$ are halogen.

5. A compound according to claim 4 wherein both $R^2$ and $R^3$ are bromine.

6. A compound according to any of claim 1, wherein $R^4$ is $C_{1-6}$-alkyl.

7. A compound according to claim 6 wherein $R^4$ is isopropyl.

8. A compound according to any one of claim 1, wherein $R^5$ is $C_{1-6}$-alkyl substituted by A, provided that A is not halogen, $C_{7-12}$-alkyl, $C_{2-12}$-alkenyl or $C_{2-12}$-alkynyl.

9. A compound according to claim 8 wherein $R^5$ is $C_{1-6}$-alkyl substituted by $(R^9)(R^{10})N$, heterocycloalkyl, aryl or heteroaryl, or $C_{7-12}$-alkyl, $C_{2-12}$-alkenyl or $C_{2-12}$-alkynyl.

10. A compound according to any one of claim 1, wherein $R^6$ is aryl.

11. A compound according to claim 1 wherein $R^6$ is heteroaryl.

12. A compound according to any one of claim 1, wherein $R^9$ and $R^{10}$ are independently of each other hydrogen or $C_{1-6}$-alkyl, or where any pair of $R^9$ and $R^{10}$ together with the nitrogen to which they are bound form a ring having 5–6 ring members.

13. A compound according to claim 1 said compound being:

3,5-Dibromo-4-[5-isopropyl-2-(3-methylbenzoyl)-4-(3-methyl-3-butenyloxy)phenoxy]phenylacetic acid (E1);

3,5-Dibromo-4-[5-isopropyl-2-(3-methylbenzoyl)-4-(2-propynyloxy)phenoxy]phenyl acetic acid (E2);

3,5-Dibromo-4-[5-isopropyl-2-(3-methylbenzoyl)-4-(pent-3-ynyloxy)phenoxy]phenylacetic acid (E3);

3,5-Dibromo-4-[4-(2-methoxyethoxy)-5-isopropyl-2-(3-methylbenzoyl)phenoxy]phenylacetic acid (E4);

3,5-Dibromo-4-[4-(2-{2-methoxyethoxy}ethoxy)-5-isopropyl-2-(3-methylbenzoyl)phenoxy]phenylacetic acid (E5);

3,5-Dibromo-4-[4-(2-{2-[2-methoxyethoxy]ethoxy}ethoxy)-5-isopropyl-2-(3-methyl-benzoyl)-phenoxy]phenylacetic acid (E6);

3,5-Dibromo-4-[4(7-hydroxyheptyloxy)-5-isopropyl-2-(3-methylbenzoyl)phenoxy]phenylacetic acid (E7);

3,5-Dibromo-4-[(2-ethylthioethoxy)-5-isopropyl-2-(3-methylbenzoyl)phenoxy]phenylacetic acid (E8);

3,5-Dibromo-4-[4-carboxymethoxy-5-isopropyl-2-(3-methylbenzoyl)phenoxy]phenylacetic acid (E9);

3,5-Dibromo-4-[4-(5-carboxypentoxy)-5-isopropyl-2-(3-methylbenzoyl)phenoxy]phenylacetic acid (E10);

3,5-Dibromo-4-[4-benzyloxy-5-isopropyl-2-(3-methylbenzoyl)phenoxy]phenylacetic acid (E11);

3,5-Dibromo-4-[4-(2-fluorobenzyloxy)-5-isopropyl-2-(3-methylbenzoyl)phenoxy]phenylacetic acid (E12);

3,5-Dibromo-4-[4-(3-fluorobenzyloxy)-5-isopropyl-2-(3-methylbenzoyl)phenoxy]phenylacetic acid (E13);

3,5-Dibromo-4-[4-(4-fluorobenzyloxy)-5-isopropyl-2-(3-methylbenzoyl)phenoxy]phenylacetic acid (E14);

3,5-Dibromo-4-[5-isopropyl-2-(3-methylbenzoyl)-4-(3-methylbenzyloxy)phenoxy]phenylacetic acid (E15);

3,5-Dibromo-4-[4-(4-tert-butoxybenzyl)-5-isopropyl-2-(3-methylbenzoyl)phenoxy]phenylacetic acid (E16);

3,5-Dibromo-4-[5-isopropyl-2-(3-methylbenzoyl)-4-(4-(trifluoromethoxybenzyloxy)-phenoxy]phenylacetic acid (E17);

3,5-Dibromo-4-[5-isopropyl-2-(3-methylbenzoyl)-4-(3-nitrobenzyloxy)phenoxy]phenylacetic acid (E18);

3,5-Dibromo-4-[4-(4-carboxybenzyloxy)-5-isopropyl-2-(3-methylbenzoyl)phenoxy]phenylacetic acid (E19);

3,5-Dibromo-4-[4-(4-carbomethoxybenzyloxy)-5-isopropyl-2-(3-methylbenzoyl)phenoxy]phenylacetic acid (E20);

3,5-Dibromo-4-[4-(3,5-difluorobenzyloxy)-5-isopropyl-2-(3-methylbenzoyl)phenoxy]phenylacetic acid (E21);

3,5-Dibromo-4-[4-(4-bromo-2-methoxybenzyloxy)-5-isopropyl-2-(3-methylbenzoyl)phenoxy]phenylacetic acid (E22);

3,5-Dibromo-4-[4-(2-chloro4,5-{methylenedioxy}benzyloxy)-5-isopropyl-2-(3-methyl-benzoyl)phenoxy]phenylacetic acid (E23);

3,5-Dibromo-4-[5-isopropyl-2-(3-methylbenzoyl)-4-(4-pyridinylmethoxy)phenoxy]phenylacetic acid (E24);

3,5-Dibromo-4-[5-isopropyl-2-(3-methylbenzoyl)-4-(2-{4-methyl-5-thiazolyl}ethoxy)phenoxy]phenylacetic acid (E25);

3,5-Dibromo-4-[5-isopropyl-2-(3-methylbenzoyl)-4-(3-phenyl -2-propenyloxy)phenoxy]phenylacetic acid (E26);

3,5-Dibromo-4-[5-isopropyl-2-(3-methylbenzoyl)-4-(4-phenylbutyloxy)phenoxy]phenylacetic acid (E27);

3,5-Dibromo-4-[5-isopropyl-2-(3-methylbenzoyl)-4-(2-{N-piperidino}ethoxy)phenoxy]phenylacetic acid (E28); or 3,5-Dibromo-4-[5-isopropyl-2-(3-methylbenzoyl)-4-(2-{N-morpholino}ethoxy)phenoxy]phenylacetic acid (E29);

or pharmaceutically acceptable salts, stereoisomers or prodrugs thereof.

14. A pharmaceutical composition comprising a compound according to claim 1, together with a pharmaceutical diluent or carrier.

* * * * *